US010265345B2

(12) United States Patent
Lau

(10) Patent No.: US 10,265,345 B2
(45) Date of Patent: Apr. 23, 2019

(54) USE OF EXTRACTS FROM RABBIT SKIN INFLAMED BY VACCINIA VIRUS FOR THE MANUFACTURE OF A MEDICAMENT FOR THE TREATMENT OF ACUTE CEREBROVASCULAR DISEASE

(75) Inventor: Mansang Lau, Hong Kong (CN)

(73) Assignee: Vanworld Pharmaceutical (Rugao) Co., Ltd., Rugao (CN)

( * ) Notice: Subject to any disclaimer, the term of this patent is extended or adjusted under 35 U.S.C. 154(b) by 0 days.

(21) Appl. No.: 13/128,254

(22) PCT Filed: Oct. 23, 2009

(86) PCT No.: PCT/CN2009/001181
§ 371 (c)(1),
(2), (4) Date: Jul. 6, 2011

(87) PCT Pub. No.: WO2010/054531
PCT Pub. Date: May 20, 2010

(65) Prior Publication Data
US 2011/0268814 A1 Nov. 3, 2011

(30) Foreign Application Priority Data
Nov. 11, 2008 (CN) .......................... 2008 1 0176703

(51) Int. Cl.
*A61K 35/36* (2015.01)
(52) U.S. Cl.
CPC .................... *A61K 35/36* (2013.01)
(58) Field of Classification Search
None
See application file for complete search history.

(56) References Cited

U.S. PATENT DOCUMENTS

| 4,985,254 | A | * | 1/1991 | Konishi | .................. | 424/520 |
| 5,013,558 | A | * | 5/1991 | Konishi | .................. | 424/520 |
| 2006/0051375 | A1 | | 3/2006 | Cheung | | |

FOREIGN PATENT DOCUMENTS

| CN | 1159324 | A | 9/1997 |
| CN | 1187369 | A | 7/1998 |
| CN | 1205233 | A | 1/1999 |
| CN | 1254597 | A | 5/2000 |
| EP | 0348353 | A2 | 12/1989 |
| EP | 0953352 | A1 | 11/1999 |
| EP | 1669082 | A1 | 6/2006 |
| EP | 2011505 | A1 | 1/2009 |
| JP | H01319422 | A | 12/1989 |
| JP | H082225452 | A | 9/1996 |
| JP | 2000016942 | A | 1/2000 |
| JP | 2001058950 | A | 3/2001 |
| JP | 2006182754 | A | 7/2006 |
| WO | WO-2007114230 | A1 | 10/2007 |

OTHER PUBLICATIONS

Dawson et al., "Cerebralvascular Hemodynamics and Ischemic Tolerance: Lipopolysaccharide-Induced Resistance to Focal Cerebral Ischemia Is Not Due to Changes in Severity of the Initial Ischemic Insult, but Is Associated With Preservation of Microvascular Perfusion", Journal of Cerebral Blood Flow and Metabolism, 1999, vol. 19, pp. 616-623.*
Chen et al., "A Comparison between Neurotropin and Enzaishi with respect to their Effects in Combating Brain lschemia and relieving Pain in Murine", Herald of Medicine, Feb. 2007, vol. 26, Journal II, pp. 1-7.*
Maier, C.M., et al., "Optimal Depth and Duration of Mild Hypothermia in a Focal Model of Transient Cerebral Ischemia: Effects on Neurologic Outcome, Infarct Size, Apoptosis, and Inflammation • Editorial Comment: Effects on Neurologic Outcome, Infarct Size, Apoptosis, and Inflammation", Stroke Journal of the American Heart Association, 1998, 29:2171-2180.
Bederson, J.B. et al, "Rat middle cerebral artery occlusion: evaluation of the model and development of a neurologic examination", Stroke Journal of the American Heart Association, 1986, 17:472-476.
Belayev, L. et al., "Middle Cerebral Artery Occlusion in the Rat by Intraluminal Suture", Stroke, 1996, 27:1616-1623.
Bederson, J.B. et al., "Evaluation of 2,3,5-triphenyltetrazolium chloride as a strain for detection and quantification of experimental cerebral infarction in rats", Stroke Journal of the American Heart Association, 1986, 17:1304-1308.
Bradford, Marion M., "A Rapid and Sensitive Method for the Quantitation of Microgram Quantities of Protein Utilizing the Principle of Protein-Dye Binding", Analytical Biochemistry 72, 1976, 248-254.
Okawa, M. et al., "DPPH (1,1-Diphenyl-2-Picrylhydrazyl) Radical Scavenging Activity of Flavonoids Obtained from Some Medicinal Plants", Biol. Pharm. Bull. 24(10) 2001, 1202-1250.
Emerich, D.F et al., "The Role of Leukocytes Following Cerebral Ischemia: Pathogenic Variable or Bystander Reaction to Emerging Infarct?", Experimental Neurology 173, 2002, 168-181.
Leizhimeing et al., "Determination of the proliferation of lymphocyte by MTT color reaction assay using 721 spectrophotometer", Current Immunology, 1990; 10(3) 172.
Itoh, et al., "Neuroprotective effects of an extract from the inflamed skin of rabbits inoculated with vaccinia virus on glutamate-induced neurotoxicity in cultured neuronal cell line", Neurological Research, May 2008, vol. 30, 430-434.
Qiu,Fuen,"International Search Report" for the International Applicaton PCT/CN2009/001181 dated Jan. 28, 2010, (6 pages).
Zhai, Yu et al., "Observation on Treatment of Neurotropin to Ischemic Stroke". Acta Universitatis Medicinalis Secondae Shanghai. Sep. 2002, vol. 22, No. 5, pp. 450-452.
Koroshetz WJ, and Moskwotz MA. "Emerging treatments for stroke in humans", Trends Pharmacol Sci. 1996, 17(6): 227-233.
Higashida RT, et al., "Trial design and reporting standards for intraarterial cerebral thrombolysis for acute ischemic stroke", Stroke. 2003, 14: 493-494.
Feng YP, "Pathophysiology of ischemic stroke and status of drug intervention", Acta Pharm Sin. 1999, 34:1, 72-78.

(Continued)

*Primary Examiner* — Laura Schuberg
(74) *Attorney, Agent, or Firm* — Winstead PC

(57) ABSTRACT

The present invention provides a method for treatment of acute cerebrovascular diseases, and also provides the use of the extracts from rabbit skin inflamed by vaccinia virus in the manufacture of a medicament for treatment of acute cerebrovascular diseases.

11 Claims, 1 Drawing Sheet

(56) References Cited

OTHER PUBLICATIONS

Fisher M, et al., "Further evolution toward effective therapy for acute ischemic stroke", JAMA. Apr. 22/29, 1998, 279:16, 1298-1303.

Longa, EZ, "Reversible middle cerebral artery occlusion without craniectomy in rats". Stroke. 1989, 20: 84-91.

Mao, Jianhua, "Observation on Treatment of Neurotropin to Ischemic Stroke", Hebei Medicine, Jan. 2005, vol. 11, No. 1, pp. 53-56.

Chen, Ji. et al, "A Comparison between Neurotropin and Enzaishi with Respect to their Effects in Combating Brain Ischemia and Relieving Pain in Murine's", Herald of Medicine, Feb. 2007, vol. 26, No. 2, pp. 149-152.

Dereuck Ja. et al., "A Double-Blind Study of Neurotropin in Patients with Acute Ischemic Stroke", Acta Neurologica Scandinavica, May 1994, vol. 89, No. 5, pp. 329-335.

Dereuck, J. et al., "Neurotropin Treatment of Brain Edema Accompanying Acute Middle Cerebral-Artery Infarction", Acta Neurochirurgica, 1994, Suppl. 60, pp. 332-334.

Ping, YP, "The pathophysiology of ischemic stroke and drug treatment status", Acta Pharm Sin. 1999, 34:1, 20 pages.

Sprumont, Pierre et al., "Effect of neurotropin on cerebral edema, calcium and other elements in mice subarachnoidally injected with carrageenan", European Journal of Pharmacology, vol. 274, No. 1-3, Feb. 1, 1995, pp. 95-99.

Kita, T et al., "Effect of neurotropin on SART stress (stress caused by alteration of rhythms in environmental temperature) in mice and rats", Medline, Mar. 1, 1975, 1 page.

Chen, Z. et al., "The Extract of Inflamed Rabbit Skin Induced by Inoculation of Vaccinia Virus Possesses Antioxidant and Neuroprotective Effects in Acute Ischemic Stroke", Journal of Stroke and Cerebrovascular Diseases, Demos Publications, vol. 18 No. 6, Nov. 1, 2009, pp. 475-481.

Gabrielian, Emil S., et al.; "Cerebrovascular Injuries Induced by Activation of Platelets and Leukocytes In Vivo and their Correction by Neurotropin"; Japan J. Pharmacol, vol. 60 (1); Sep. 1992; pp. 51-54.

Journal of Guangxi Medical University; vol. 3; Jun. 25, 2008; pp. 434-435.

Kekkan Igaku; Vascular Biology & Medicine, vol. 7, No. 5; May 2006; pp. 33-38.

Katayama, Yasuo; "Current Tendency in Treatment for Acute Ischemic Stroke"; Nippon Ika Daigaku Zasshi 66(3); Jun. 1999; pp. 160-165.

\* cited by examiner

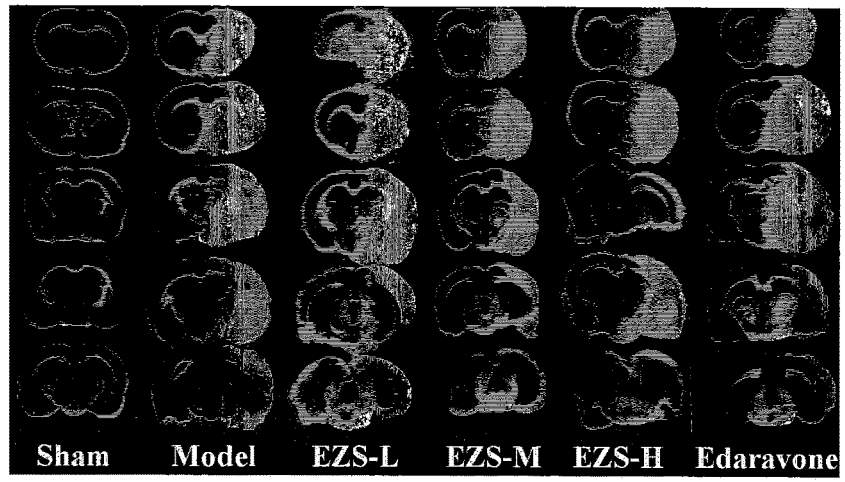
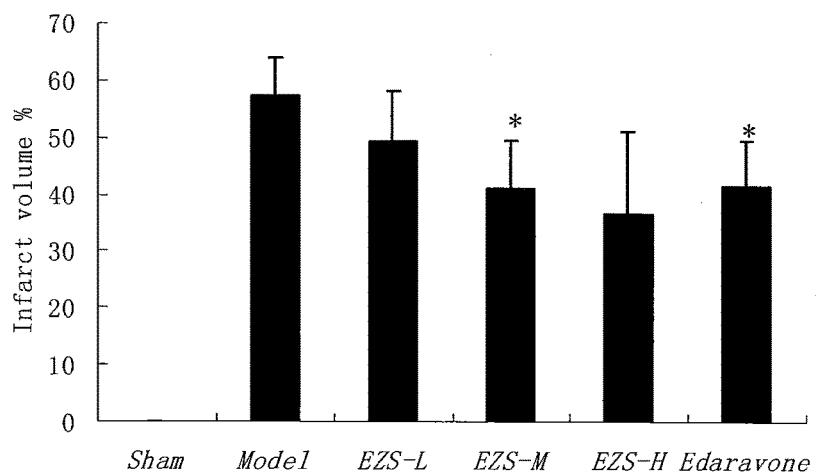
Effects of analgecine on the volume of cerebral infarction 48 hours after permanent MCAO. The values were expressed as percentage of volume (means ± SD) for 3 animals per group. Sham: sham group. Model: model group. Analgecine-L: low-dose analgecine; Analgecine-M: mid-dose analgecine; Analgecine-H: high-dose analgecine. *$P<0.05$ compared to model group.

USE OF EXTRACTS FROM RABBIT SKIN INFLAMED BY VACCINIA VIRUS FOR THE MANUFACTURE OF A MEDICAMENT FOR THE TREATMENT OF ACUTE CEREBROVASCULAR DISEASE

FIELD OF THE INVENTION

This invention relates to the treatment of acute cerebrovascular diseases. In particular, it relates to extracts from rabbit skin inflamed by vaccinia virus in the manufacture of a medicament for treating acute cerebrovascular diseases.

BACKGROUND OF THE INVENTION

Stroke, one of the acute cerebrovascular diseases, is the third leading cause of death in worldwide population and induces a highest disabling rate among various diseases. As indicated by the recent epidemiology references, the incidence of cerebrovascular diseases in China ranges from about 0.12% to 0.18%, which is the second cause among population death. There are 1.2 to 1.5 millions peoples newly developed cerebrovascular diseases each year, and 0.8 to 1 millions patients died, about 75% of survivals were disabled, and relapse rate within 5 years was up to 41%. The cerebrovascular diseases could severely affect the life quality of the elderly, bring an enormous burden to patients' family and the society. It also trends to increase in young population.

The cerebrovascular diseases are primarily classified into two types, hemorrhagic and ischemic, of which the latter is 60-70%, and is the most common type of cerebrovascular diseases. It is important to study the pathophysiological mechanism of ischemic cerebrovascular diseases and search for drugs which function as neuroprotection.

The research of the pathophysiologic mechanism of cerebral ischemia has been one of the most focuses of the neuroscience field since 1980s, and so far theories of cerebral ischemia concerning such as energy metabolism, acid intoxication, peroxidation injury, excitatory amino acid induced toxicity injury and calcium overload have been proposed, in which the last two play an important role in ischemic neuronal injury and death. According to pathophysiologic basis of ischemic cerebrovascular diseases, drugs currently used to clinically treat cerebral ischemia mainly comprise calcium ion antagonists (nimodipine), oxygen radical scavengers (VitE, SOD), neurotrophic factors (nerve growth factor, neurotrophic factor), excitatory amino acid antagonists, antioxidants and drugs which improve late-onset neuronal injury. These drugs function via various mechanisms of action, with uncertain therapeutical effects or less specificity or with the concomitancy of severe side-effects, and thus can not fulfill the clinical requirements yet. There are many commercially available drugs which can be used to improve cerebral circulation, metabolism and functions, such as piracetam, flunarizine, calan, ginkgo extracts. Although they all have certain characteristics, the treatment effects thereof on cerebrovascular diseases are uncertain. Research and development of novel drugs for treating ischemic cerebrovascular diseases is an important task in the field of pharmaceutics and pharmacology.

As used herein, "the extracts from rabbit skin inflamed by vaccinia virus" refers to the active substances extracted from the rabbit skin inflamed by vaccinia virus, as described in Chinese patent NO. ZL98103220.6, the entirety of which is incorporated herein by reference. Such extracts from rabbit skin inflamed by vaccinia virus are commercial available, with trade name of analgecine, which is manufactured by Vanworld Pharmaceutical (Rugao) Co. Ltd. The pharmacological effects of analgecine include: (1) analgesic effects, including obvious analgesic effects on hyperalgesia complexly induced by repeated cold stresses, which are achieved by activating the descending inhibition system of central nervous system; (2) effects on sense of coldness and abnormal perception: it has been showed by experiments in vivo and in vitro that such agent has the effects of changing the neuron sporadic activity of hypothalamus, suggesting that the agent has reparative and regulating effects on abnormal sense neuron sporadic activity, which is considered to be the cause for neuralgia and abnormal perception; (3) effects of improvement of peripheral blood circulation; (4) effects on regulation of autonomic nerves: it has been suggested by the experiment in vivo and in vitro that the agent can improve the symptoms of autonomic nerve system dysregulation by regulating the activity of central autonomic nerve; (5) effects on anti-allergic reaction: it has been suggested by animal experiments that the agent has effects on anti-allergic reaction type I, which has inhibitory effects on respiratory tract hypersecretion resulted from excitation of parasympathetic nerve, and also has inhibitory effects on up-regulating the density of nasal mucosa receptor M; (6) effects of sedation: it has been suggested by animal experiments that the agent has a sedative effect on the affective excitation state caused by various external stimulations.

Furthermore, the extracts from rabbit skin inflamed by vaccinia virus were discussed in the following applications: Chinese patent application NO. 99123485.5, filed on Nov. 12, 1999; Chinese patent application NO. 96123286.2, filed on Dec. 19, 1996; and Chinese patent application NO. 98103914.6, filed on Jan. 7, 1998.

However, the protective effects of analgecine on cerebral ischemia injury have not been reported yet. The present invention has investigated such effects, and found that analgecine has a beneficial effect on cerebral ischemia in the experimental animal models.

DESCRIPTION OF THE INVENTION

In one aspect, the present invention provides a method for treating acute cerebrovascular diseases in mammals comprising administrating to a subject in need of thereof such extracts from rabbit skin inflamed by vaccinia virus.

In another aspect, the present invention provides the use of the extracts from rabbit skin inflamed by vaccinia virus for the manufacture of a medicament for treating acute cerebrovascular diseases in a mammal.

In one embodiment, the acute ischemic cerebrovascular diseases as described herein are acute ischemic cerebrovascular diseases.

Cerebrovascular diseases are neural function injuries caused by abnormal blood supply of regional brain. In most countries, cerebrovascular diseases, the top three causes of all deaths, can result in a brain injury in adult. Cerebrovascular disease is a major cause for endangering the health of the middle-aged and the aged people, and a major cause of death or disability of the middle-aged and the aged people in most countries. Ischemic cerebrovascular diseases mostly resulted from cerebrovascular occlusion, which is generally known as embolism or thrombosis; and its pathophysiology changes are highly complicated. In one embodiment, the acute ischemic cerebrovascular diseases as described herein include, but not limited to cerebral embolism, transient cerebral ischemia attack, cerebral thrombosis, cerebral arteriosclerosis, cerebral arteritis, steal syndrome of cerebral artery, cranial venous sinus and venous thrombus.

Ischemic cerebrovascular disease is caused by transient or permanent reduction of blood flow in certain areas of artery blood supply due to embolism, and its pathological processes relate to complicated temporal and spatial cascade reaction. The pathophysiologic mechanism of cerebral ischemia has been widely investigated in recent years. However, the direct reason of this disease is that each artery has its basic ranges of blood supply in the brain, and the occlusion of the artery will lead to softening of the brain tissues in the respective areas, resulting in the corresponding clinical syndromes, in which the neurological symptomatologic injuries (such as contralateral limb hemiplegia) caused by middle cerebral artery occlusions are the most common. Furthermore, in the clinical cases of first onset of stroke, the percentage of the middle cerebral artery obstructions is large, so the pathological processes simulated by an animal model of middle cerebral artery obstruction (MCAO) have great similarity to that of clinical strokes.

The results of Bederson's scoring and a slope test have shown that the signs of neurological symptomatology injuries, such as contralateral limb weakness and paralysis, occurred after ischemia of brain tissues in rats. The present inventors have found that analgecine can remarkably improve the neurological symptoms of animals. Therefore, in one embodiment, analgecine can be used for the treatment of cerebrovascular diseases by improving the neural function.

The areas of cerebral infarction foci are related to the extent of ischemia, TTC staining of the contralateral brain tissues showed white, and liquefying foci could be observed 24 hrs after unilateral middle brain artery embolization. The results of statistical analysis showed that there was statistically significant difference in the volume of cerebral infarction in a sham group in comparison to a solvent group, and the volume of cerebral infarction in a mid-dose analgecine group significantly decreased as compared to that of an injury group. Therefore, in one embodiment, analgecine is used for treatment of cerebrovascular diseases by reducing the areas of cerebral infarction.

Brain is the most active organ in metabolism with the least energy and oxygen storage per se. The consumed oxygen of the brain tissues accounted for 20% of total body oxygen consumption under the resting state. Neurons constitute the primary parts which consume oxygen in the cerebral cortex or whole brain, and are highly sensitive to ischemia and hypoxia injury. When there is no source of fresh oxygen, the tissues can only consume their high energy phosphate compound storage, and obtain the energy by means of metabolising the stored glucoses and glycogens into MDA. The ischemia and/or hypoxia of the brain tissues leads to energy exhaustion, resulting in a series of chain reactions including failure to energy pump function, calcium ion overload within nerve cells, increase of toxic oxygen radical, cellular acid intoxication; and the structure of cell membrane and integrality are damaged, as a result, the permeability of the membranes increases, the extents of cytotoxic edema expand, and some intracellular enzymes are largely released into the blood. The results showed that the level of lactic acid and MDA in brain tissues significantly increased after ischemia, whereas the level of lactic acid in brain tissues significantly decreased via intervention with analgecine. Therefore, in one embodiment, analgecine is used for treatment of cerebrovascular diseases by decreasing the level of lactic acid in brain tissues.

SOD is an important antioxydant enzyme which can inhibit free radical reactions effectively, and high SOD activities represent strong antioxydant abilities. The SOD activities of the brain tissues in rats decreased significantly and accordingly the abilities of free radicals elimination decreased after cerebral ischemia injuries. The results showed that the SOD activities can be enhanced via intervention of analgecine, indicating that analgecine may play a role in neuroprotection by increasing the antioxidant abilities of brain tissues. Accordingly, in one embodiment, analgecine is used for treatment of cerebrovascular diseases by increasing the SOD activities.

In another aspect, the present inventor discovered that analgecine can have a protective effect on nerve cell injury.

$H_2O_2$ is an important reactive oxygen component which is involved in the onset of nervous system diseases such as cerebral ischemia, trauma, brain aging, Alzheimer's disease etc. It will peroxidate membrane lipid, decrease cell membrane fluidity, change components and activities of intracellular proteins, make chromatin concentrated and DNA broken, and finally result in cell death. Therefore, in one embodiment, analgecine is used to improve $H_2O_2$-induced injury of PC12 cell.

Excitatory amino acids, such as glutamic acid, played an important role in the course of a variety of chronic or acute neuropathy which will be accompanied by neuronal death. Glutamic acid can damage nerve cell line and primary nerve cell in dose dependent manner. It is responsible for the increased intracellular calcium ion and the blocked cystine uptake, and it induces the loss of intracellular reduced glutathione (GSH), the increased oxygen radical and nerve cell death. Therefore, $H_2O_2$ or glutamic acid-induced nerve cell injury model can be used as a screening model of neuroprotective agents. Therefore, in one embodiment, analgecine is useful to improve glutamic acid-induced injury of PC12 cell, inhibit the expression or excretion of ICAM-1 in endothelial cell of the brain vessels, and/or inhibit T- and B-lymphocyte transformations.

T-lymphocytes exhibits increased cell volume, robust metabolism, increased synthesis of protein and nucleic acid, and be able to achieve lymphoblast divisions after stimulated by specific antigen or nonspecific mitogen during culturing in vitro. The level of lymphocyte transformation rate reflects the immunologic function of cells in individuals. Therefore, lymphocyte transformation test is widely used for determining one of the indicators of immunologic functions of the cells in an individual, and also for screening immunomodulators. The experiment studies have found that analgecine has certain inhibitory effects on lymphocyte transformation. Therefore, in one embodiment, analgecine is useful to inhibit the transformations of T- and B-lymphocytes.

The inner membranes of vessels, which are made of endothelium consisted of endothelial cells, play an important role in maintaining vessel homeostasis. Functions of endothelial cells can be easily affected by ingredients in the blood because such cells are in contact with the blood directly. The endothelial cells are activated under the pathological conditions, such as hypoxia, chronic and acute inflammation, ischemia injury, and in turn express some adhesion molecules: ICAM-1 (intercellular adhesion molecule-1), VCAM-1 (vascular cell adhesion molecule-1), E-selectin and P-selectin. Adhesion molecules play an important role in pathological processes of blood vessel endothelium and vessel, wherein ICAM-1 plays a key role in the close adhesion of leukocyte to endothelium. Therefore, in one embodiment, analgecine is useful to inhibit endothelial cells in cerebral vessels to express or excrete ICAM-1.

The present invention relates to an analgesic and its manufacturing method. The analgesic is produced by preparing an active agent from pox skin tissue of rabbit and mixing the active agent with a pharmaceutically acceptable excipient, wherein the active agent is prepared by the steps of inoculating rabbit with vaccinia virus, extraction in solvent, acid treatment, alkaline treatment, absorption, rinsing, concentration and so forth.

An analgesic is a class of drug that acts primarily on the central nervous system and selectively inhibits pain without affecting the sensation. Opioid alkaloids and their synthetic substitutes are the typical centrally-acting analgesics. They have strong analgesic effect, but their side effects are very serious and repeated dosage can cause addiction, tolerance, and respiratory depression. Hitherto, there has been no clinically potent analgesic with minimal side effects.

Therefore, the present invention is to provide an analgesic with strong analgesic effect, and minimal side effects and a method for manufacturing such analgesic.

The analgesic of the present invention contains an active agent and a pharmaceutically acceptable excipient, wherein said active agent contain aspartic acid, threonine, serine, glutamic acid, glycine, alanine, valine, isoleucine, leucine, tyrosine, phenylalanine, lysine, histidine, urocanic acid, uracil, hypoxanthine, xanthine, and thymine. The substances mentioned above ranging in (µg/ml) are: 0.2-0.5 aspartic acid, 0.1-0.4 threonine, 0.3-0.8 serine, 0.7-1.4 glutamic acid, 0.3-0.7 glycine, 0.4-0.9 alanine, 0.1-0.4 valine, 0.1-0.3 isoleucine, 0.1-0.4 leucine, 0.2-0.6 tyrosine, 0.1-0.4 phenylalanine, 0.05-0.2 lysine, 0.1-0.4 histidine, 12.0-22.5 urocanic acid, 6.5-12.1 uracil, 0.7-1.4 hypoxanthine, 5.4-10.2 xanthine, and 1.3-2.5 thymine. This preparation is a colorless or pale yellow liquid with pH value of 7.0-8.0, UV absorption at 265-275 nm, positive in ninhydrin reaction, negative in test for various proteins, positive in 3,5-dihydroxy toluene-hydrochloric acid reaction, and positive in arsenomolybdate color reaction. The active agent is prepared by the steps of:

a) collecting a pox skin tissue from vaccinia virus (Vaccinum variolae) Lister strain-inoculated rabbit;

b) cutting the collected tissue into small pieces, to which 2.5 to 3.5 times the amount of 2% phenol aqueous solution is added, and obtaining a solution A by soaking, centrifugation and filtration;

c) obtaining a solution B by adjusting the solution A to weak acidity, boiling and then centrifugation and filtration;

d) obtaining a solution C by adjusting the solution B to weak alkalinity, and boiling followed by filtration;

e) obtaining a solution D by adjusting the solution C to weak acidity, to which an adsorbent is added, and soaking, filtration, and eluting the adsorbent with water in an alkaline environment;

f) obtaining a solution E by adjusting the solution D to weak acidity, and heating following by cooling;

g) concentrating the solution E under reduced pressure and filtration.

Preferably, the active agent is prepared by the steps of:

a) collecting the pox skin tissue from vaccinia virus Lister-inoculated rabbit;

b) cutting the collected tissue into small pieces, to which 3-fold amount of 2% phenol aqueous solution is added, and obtaining a solution A by soaking for 72 hours, centrifugation and filtration;

c) obtaining a solution B by adjusting the solution A to pH 5.0, boiling for 30 minutes and then centrifugation and filtration;

d) obtaining a solution C by adjusting the solution B to pH 9.2, boiling for 30 minutes followed by filtration;

e) obtaining a solution D by adjusting the solution C to pH 4.5, to which activated charcoal is added, and soaking for 4 hours, filtration and eluting the activated charcoal with water under pH 11.0;

f) obtaining a solution E by adjusting the solution D to pH 6.0, heating to 121° C. and then cooling to below 40° C.;

g) concentrating the solution E under reduced pressure at 60° C., and then filtration.

After obtaining the active agent, the analgesic of the present invention is obtained by mixing the active agent with a pharmaceutically acceptable excipient. The analgesic can be used in different clinical application with various pharmaceutical forms such as injection, tablet, ointment, capsule, granule, and so forth. It is preferable to use injection form. The pharmaceutically acceptable excipient includes various pharmaceutically acceptable carriers. For injection, the excipient can be distilled water for injection, normal saline, vegetable oil for injection, glucose injection, propylene glycol, polyethylene glycol, and so forth. The excipient can also be various stabilizers, emulsifiers and so forth. For tablet, capsule and granule forms, the excipient can be adjuvant such as starch, lactose, mannitol and so forth; binding agent such as crystalline cellulose, acacia, corn starch, gelatin, polyethylene, polyvinyl alcohol, polyvinyl pyrrolidone and so forth; disintegrant such as carboxymethyl cellulose, polyethylene glycol, potato starch; lubricant such as talcum powder, magnesium stearate and so forth; wetting agent such as glycerol and so forth. In ointment form, the excipient can be fatty oil, paraffin, lanolin, petrolatum, ethylene glycol, glycerin and so forth as substrate.

Pharmacological and clinical studies show that the analgesic of the present invention has analgesic effect on various diseases. The diseases include various neuralgia, low back pain, biliary colic, angina, arterial embolization pain, severe pain caused by various reasons such as trauma and burns, intra-operative and post-operative pain, pain due to peptic ulcer diseases, dysmenorrhea, pain due to uterine contractions after childbirth, headache, pain caused by cancer or tumor, and so forth. Furthermore, the analgesic of the present invention can improve immune functions. Additionally, the analgesic of the present invention has minimal side effects.

Using a reduced pain-threshold animal model for autonomic nervous system disorders, the study with specific alternation of rhythm in temperature (SART)-stressed rat via both the thermal stimulation by Thamr-Smith method or mechanical stimulation by Randall-Selitto method have confirmed that the analgesic of the present invention has significant analgesic effect on this rat model of autonomic nervous system disorders.

Clinically, the analgesic of the present invention was tested on 20 patients with cutaneous pruritus. The analgesic of the present invention was injected subcutaneously daily with 1 ampule (3 ml), at least 3 times a week, for 2 weeks. At the end of the treatment, 70% of the subjects had complete or moderate improvement while 95% of tested subjects had mild or better improvement. In a clinical trial with 29 patients with low back pain, it was shown that muscle and subcutaneous injection of the analgesic of the present invention is effective and safety for pain relief.

The study using immune related inflammation as indicator with consideration of 48 hours autologous PCA inhibition activity, and anti-complement activity acting on macrophages showed that the analgesic of the present invention could effectively promote the activation of macrophages, significantly inhibit the IgE antibody production and the related 48-hr autologous PCA reaction in mouse model of type I allergic reaction, and suppress anti-complement activity in type II allergic response model. The relationship between effect and dosage was linear. Therefore, the analgesic of the present invention can suppress the inflammation related to the immune function and, in turn, improve immune functions.

The acute toxicity of the analgesic of the present invention was tested in mouse and rat model with a single oral or intraperitoneal or subcutaneous administration. The dosage for intraperitoneal and subcutaneous administration was 6,000 unit/kg while the dosage for oral administration is 10,000 unit/kg. During the 14-day observation period, there was on one male death in the subcutaneous administration group while all animals were survived in other groups. The one in the subcutaneous administration group died at day 5 after drug administration. After autopsy examination, no abnormality was observed. Therefore, it was not confirmed that the drug caused the death. In the chronic toxicity test, the rats were intraperitoneally administrated with the analgesic of the present invention at dosages of 30, 60, 120 unit/kg for 28 days. No death was observed. The examinations of urine, eye, hematology, histopathology, and anatomy showed that the analgesic of the present invention did not cause any pathological changes. Therefore, the analgesic of the present invention has very low toxicity.

The antigenic activity experiment in guinea pigs and mice showed that the analgesic of the present invention had no antigenic activity. In a rabbit experiment, total number of injury of the gross and histopathological observation was counted as safety test indicator. The test showed that the analgesic of the present invention had very low local toxicity.

During the fetal organogenesis phase of Slc:ddy SPF mice (equivalent to gestation 6-15 days), the subcutaneous injection of the analgesic of the present invention at 3 dosages (1.2, 12, 120 unit/kg; 1 time/day) was applied to the mothers to test the effect on the animals, fetus, and the neo-natal. The results showed that the drug did not affect the maternal health status, body weight, and amount of in-take during gestation and lactation. After giving birth, the lactation and anatomical observation of the mother was found no abnormality related to the substance injected. There was no abnormality found in the appearance, skeletal system, and different organs of the fetus due to the injected test substance. It was also observed that the injected substance did not affect the survival rate, body weight changes, appearance changes, various functions during weaning, behavior, and reproduction function of neo-natal and the off-spring.

The recovery test using bacteria (*Salmonella typhimurium* TA100, TA98, TA1535, TA1537 and *Escherichia coli* WP2uvrA) showed that the analgesic of the present invention did not cause a genetic mutation observed. The chromosomal abnormality test of mammalian cell culture (CHL) showed that the analgesic of the present invention did not cause chromosome aberrations. An in vitro cytogenetic assay for micronuclei cytotoxicity was conducted on ICR (Crj:CD-1) mice and showed that no chromosome aberration was observed.

BRIEF DESCRIPTION OF DRAWING

FIG. 1. Effects of analgecine on the volume of cerebral infarction 48 hours after permanent MCAO

SPECIFIC MODE FOR CARRYING OUT THE INVENTION

Unless defined otherwise, all scientific terms used herein have the same meaning as that commonly understood by one of ordinary skill in the art. Exemplary methods and materials are described below, although the equivalents thereof can be used. All publications and other references mentioned herein are incorporated by reference in their entirety.

The present invention will now be described further with reference to the following examples which, however, are not intended to limit the scope of the present invention.

Examples 1: Protective Effects of Analgecine on Acute Cerebral Ischemia (MCAO) in Rats Experimental Materials
1. Drugs and Reagents
10 u/ml analgecine injections, 25 ml/vial (provided by Vanworld Pharmaceutical (Rugao) Co. Ltd.); 2,3,5-Triphenyltetrazolium chloride (TTC), manufactured by Sigma (American); MDA, SOD and Lactate Dehydrogenase kit, manufactured by Nanjing Bioengineering Institute.
2. Test Animals and Grouping
Male Wistar rats, weighed 280-300 g, were provided by Beijing Vitalriver Experimental Animal Center (License: SCXKjing 2007-0004). The animals were housed in conventional manner under room temperature at 23-25° C. before or after surgery, and food and water provided ad libitum.

The rats were randomized into 6 groups: sham group, injury model group (vehicle control), analgecine dosing group (10 u/kg, 20 u/kg, 40 u/kg), edaravone dosing group (3 mg/kg). The drugs were administrated to the animals 5 times starting 2 hrs after surgery (2 h, 6 h, 20 h, 24 h, 47 h). The animals were sacrificed 48 hours after surgery, and then each test was conducted.
Experimental Methods
1: Preparation of a Rat Model of Middle Cerebral Artery Obstruction
String inserting method was used for preparing a cerebral ischemia model with reference to the method of occlusion via string ligation for rat middle cerebral artery established by Zea Longa et al[5-6].
1.1: Preparation of Nylon String Plug
Marks were made at the starting point and 18.5 mm away from the starting point of string, which was washed with 75% (v/v) ethanol, and placed in heparinized saline at 1:2500 until use.
1.2 Pre-Surgery Anesthesia
Rats were intraperitoneally injected with 10% chloral hydrate solution at 400 mg/kg.
1.3 Surgery Processes
(1) Preparation of Surgery Visual Field:
Rats were fixed in dorsal position, and made an incision on skin just at the middle of the neck. The left common carotid artery (CCA) was exposed after layers of tissues bluntly dissected.
(2) Separation of Carotid Artery:
Internal carotid artery (ICA) was carefully separated from external carotid artery (ECA) to the last part of bifurcate point to evade injury of vagus nerve and trachea, and strings were placed for later use. Ipsilateral external carotid arteries were separated, and ligation was made at about 0.8 cm from the beginning of branching of ECA.

(3) Ligation of Middle Cerebral Artery:

A bulldog clamp was used for clamping at the proximal end of CCA, and "V" type incision about 2 mm in diameter was made between the ligation of ECA and the bifurcate point. Before the bulldog clamp was unclamped, the nylon string was gently inserted into CCA from the incision, and then was passed through the bifurcate point between internal carotid artery and external carotid artery into the internal carotid artery. The nylon string was slowly pushed towards the part of ICA in the intracranial direction for about 18.5±0.5 mm in depth until slight resisting force appeared, and then the other end of nylon string was passed through the beginning of the MCA to reach a thinner anterior cerebral artery. The blood flow blockage in left middle cerebral artery has been achieved at this moment, then the ICA was sutured to secure the nylon string and to avoid bleeding, followed by suturing in layers with 1 cm of the end of the nylon string left outside the skins. The anesthesia before surgery and vascular separation operation were only conducted in the sham group without ligating and introducing the String. Room Temperature was Maintained at 24-25° C. Throughout the Surgery Process.

2. Neuroethological Test 2.1 Bederson's Scoring

Before the animals were sacrificed, they have been observed neuroethologically according to the methods described by Bederson[7] and Belvyev[8] etc., which includes: grabbing a rat by tail about 1 chi above the ground to observe the status of both forelimbs; placing the rat on flat ground and pushing their both shoulders to observe whether there are any differences in resistance between two sides; placing the rat on the ground to observe their ambulation. Each animal was scored. All the animals were ranked into 3 grades with 10 scores in total based on the severity of symptom. A higher score represents the severer behavior disorder according to standard behavior rating.

The particular scoring method is as follows:

| Method | Symptom | Ranking | Score |
|---|---|---|---|
| 1 + 2 + 3 | Negative results of test 1, 2, 3 | 0 | 0 |
| 1. When the tail of a rat was grabbed about 1 chi above the ground, the forelimbs of the normal rat extend downward symmetrically. | The contralateral forelimbs retract with internal rotation after injury. | 1 | 1 |
| 2. Place the animal on a smooth plane and squeeze lateral sides of its body with hands respectively. | Contralateral muscle strength declines, and the animal tends to tumble towards the contralateral side after injury. | 2 | 3 |
| 3. Place the animal on the ground to observe its ambulation. | The animal rotates towards one side. | 3 | 6 |

3. Determination of the Volume of Cerebral Infarction

The rats were decapitated after being graded. The brain tissues were removed and placed in a freezer at −20° C. for 10 min, then at room temperature. After Olfactory bulb, cerebellum and lower brain stem were removed, 4 coronal incisions were made into 5 consecutive brain coronal sections at interval of 2 mm as shown in FIG. 1. The first incision was made at the middle of connection line between procerebral pole and chiasma opticum; the second was at chiasma opticum; the third was at the infundibular stalk site; and the forth was between infundibular stalk and caudate nucleus. Then the brain sections were quickly immersed in 5 ml TTC solution (containing 1.5 ml 4% TTC solution+3.4 ml distilled water+0.1 ml 1 mol/L $K_2HPO_4$ solution) on bath at 37° C. in the dark for 30 min. The sections were turned over once every 7-8 min Normal brain tissues were in rose color after staining, while infarction tissues were white and were clearly defined. The brain sections of each group were arranged in order, and the images were taken and saved. Image analysis system software was used for process and statistical analysis. The volume of cerebral infarction was determined by the sum of the products of the area of each brain section for each animal and 2 mm, the thickness of each section. Infarction volume was expressed as percentage of the volume of hemisphere in order to remove the errors caused by cerebral edema.

volume of cerebral infarction (%)=(volume of contralateral hemisphere in surgery−volume of contralateral hemisphere in surgery without infarction)/volume of contralateral hemisphere in surgery×100%

4. Determination Biochemical Indicators in Brain Tissues 4.1 Preparation of Brain Tissue Homogenate The brains were removed after the rats were decapitated. The left hemisphere was separated from the right, and 1 mm frontal pole and 1 mm occipital pole were removed. The brain tissues were placed in cold homogenization buffer (Tris-HCl 50 mmol/L, NaCl 150 mmol/L, $CaCl_2$ 5 mmol/L, PMSF 0.1 mmol/L, pH 7.4) at volume ratio of 1:10, then minced to small pieces, and homogenized at 4° C. The concentration of the protein was determined by Bradford's method[10].

4.2 Measurement of Lactate Dehydrogenase in Brain Tissues of the Rats (1) Experimental Principle The substrate, lactic acid, was catalyzed into pyruvic acid by lactate dehydrogenase in the presence of oxidized coenzyme I at pH 10, then the resulting pyruvic acid could react with 2,4-dinitrophenylhydrazine to give brownish dinitrophenylhydrazone pyruvate. The content of pyruvic acid can be determined by colorimetric assay, from which the activities of lactate dehydrogenase may be derived.

(2) Test Method

The activities of lactate dehydrogenase were determined according to the instruction in the kit. 10 µl homogenate and 10 µl 5 g·L$^{-1}$ coenzyme I were added to the buffered medium solution and incubated at 37° C. for 15 min; then 50 µl 0.2 g·L$^{-1}$ 2,4-dinitrophenylhydrazine was added, incubated at 37° C. for 15 min; 150 µl 0.4 mol/L NaOH was added and mixed, then the absorbance was read at 440 nm after calibration. The standard curve was plotted with sodium pyruvate standards.

4.3 Determination of the Activities of Superoxide Dismutase (SOD) in the Brain Tissues of Rats (1) Experimental Principle Superoxide anion radicals which were produced by xanthine and xanthine oxidase reaction system, can oxidize hydroxylamine to form nitrite which will be developed into purplish red by the chromogenic agent. The SOD in the sample specifically inhibits superoxide anion radicals, and accordingly the produced nitrite will be reduced.

(2) Test Method

Homogenization was carried out as described above. The activity of SOD was determined according to the instructions in the kit after the homogenate was well mixed. One unit of nitrite corresponds to the value when 50% inhibition of SOD was reached for each milligram protein of the tissues in 1 ml reaction solution.

5. Statistical Analysis

The results are expressed as means±SD. The data comparisons among groups were performed by t-test.

Results of Assay

1. Effects of Analgecine on Neurological Symptomatology of Acute Cerebral Ischemia in Rats Anaesthetized rats have recovered their consciousness and have developed various degrees of focal neural dysfunction after cerebral ischemia, representing as lacking strength of lower left limbs, turning left when walking upright, tumbling to the left and even not being able to walk, and even showing disorder of consciousness; when grabbed by tail, exhibiting flexion of the left forelimb, retraction, as well as extension of the hind limb and turning right. The animals in model group exhibited obvious symptoms of neural injury after cerebral ischemia with significant increase in score of neural function (P<0.01); 40 u/kg analgecine improved the neural function symptoms significantly (P<0.05), whereas 10, 20 u/kg groups had no significant effects of improvement. There was no significant difference between the edaravone group and model group. The results are shown in Table 1.

TABLE 1

Effects of analgecine on the score of MCAO neurological symptoms in rats

| Groups | Doses | Animals (n) | Scores |
|---|---|---|---|
| Sham group | — | 8 | 0 |
| Model group | — | 8 | 5.3 ± 2.8## |
| Low-dose analgecine group | 10 u/kg | 8 | 3.4 ± 2.5 |
| Mid-dose analgecine group | 20 u/kg | 8 | 3.4 ± 2.8 |
| High-dose analgecine group | 40 u/kg | 7 | 2.0 ± 2.6* |
| Edaravone group | 3 mg/kg | 6 | 4.3 ± 1.6 |

The values were expressed as means ± S.E.M., 6~8 animals per group.
P < 0.05 compared to sham group.
*P < 0.05 compared to model group.

2. Effects of Analgecine on the Volume of Cerebral Infarction of Acute Cerebral Ischemia in Rats The normal brain tissues wholly exhibited rose color after staining, whereas the infarction tissues exhibited white and were clearly defined. Except for the sham group, all the cerebral cortices of the rats in other groups exhibited obvious infarct foci and even the striatum is affected. The area of the cerebral infarction in edaravone group and mid-dose analgecine group decreased significantly. The results were shown in FIG. 1.

3. Effects of Analgecine on the Level of Lactic Acid in Acute Ischemic Brain Tissues of Rats The level of lactic acid in the brain tissues of rats increased to 0.98±0.09 mmol/g protein after ischemia injury with significant difference (P<0.01) compared to sham group; the level of lactic acid in the group of 40 u/kg analgecine decreased significantly to 0.70±0.07 mmol/g protein with statistical significance (P<0.05) compared to model group; the level of lactic acid in edaravone group decreased significantly to 0.64±0.08 mmol/g protein with statistical significance (P<0.05) compared to model group. The results are shown in Table 2.

TABLE 2

Effects of analgecine on the level of lactic acid in the brain tissues of rats 48 hours after permanent MCAO

| Groups | Doses | Animals (n) | Level of Lactic acid (mmol/g protein) |
|---|---|---|---|
| Sham group | — | 4 | 0.37 ± 0.01 |
| Model group | — | 6 | 0.98 ± 0.09## |
| Low dose analgecine group | 10 u/kg | 5 | 0.74 ± 0.14 |
| Mid-dose analgecine group | 20 u/kg | 5 | 0.88 ± 0.11 |
| High-dose analgecine group | 40 u/kg | 5 | 0.70 ± 0.07* |
| Edaravone group | 3 mg/kg | 6 | 0.64 ± 0.08* |

The values were expressed as means ± S.E.M., 4~6 animals/group.
P < 0.01 compared to sham group.
*P < 0.05 compared to model group.

4. Effects of Analgecine on the Superoxide Dismutase Activity in Brain Tissues of Rats The level of SOD in brain tissues of rats decreased to 165.84±13.14 nmol/g protein with significant difference (P<0.01) compared to sham group after ischemia injury; the level significantly increased in 20 u/kg and 40 u/kg analgecine dosing groups compared to model group (P<0.05); the level of SOD in edaravone group significantly increased compared to model group (P<0.01). The results are shown in Table 3.

TABLE 3

Effects of analgecine on SOD activity and the level of MDA in brain tissues of rats 48 hours after permanent MCAO

| Groups | Doses | Animals (n) | SOD Activity (U/mg pro) |
|---|---|---|---|
| Sham group | — | 4 | 354.17 ± 64.26 |
| Model group | — | 6 | 165.84 ± 13.14## |
| Low dose analgecine group | 10 u/kg | 5 | 198.96 ± 12.89 |
| Mid-dose analgecine group | 20 u/kg | 5 | 263.46 ± 34.86* |
| High-dose analgecine group | 40 u/kg | 5 | 268.09 ± 32.42* |
| Edaravone group | 3 mg/kg | 6 | 234.66 ± 15.85** |

The values were expressed as means ± S.E.M., 4~6 animals/group.
P < 0.05 compared to sham group.
*P < 0.05 compared to model group.

Examples 2: Effects of Analgecine on H2O2-Induced PC12 Cell Injury

Experimental Materials

1. Drugs and Reagents

PC12 cells were purchased from Institute of Basic Medical Sciences of Chinese Academy of Medical Sciences; 3-(4,5-Dimethylthiazol-2-yl)-2,5-diphenyltetrazolium bromide (MTT), trypsase, polylysine, standard fetal bovine serum (FBS), 1640 medium, LDH kit (available as above). All other conventional reagents are analytically pure reagents commercially available in China.

2. Instruments

Super clean bench; Fluostar microplate reader (BMG, Germany); Cell incubator (Sanyo, Japan); Refrigerated centrifuge DL-4000B (Shanghai Anting Scientific Instrument Factory); and Microscope IX71 (OLYMPUS).

Experimental Method

1. PC12 Cell Culture

PC12 cells provided by Institute of Basic Medical Sciences of Chinese Academy of Medical Sciences were cultured in complete 1640 medium (containing 10% equine serum, 5% fetal bovine serum, 100 U/ml penicillin, 100

μg/ml streptomycin) at 37° C. and 5% CO2 in a thermostatic incubator with the medium changed every 2-3 days[6].

2. Cell Processing

Normal control group: PC12 cells were normally cultured in serum-containing DMEM medium; H2O2 model group: the original media were removed after PC12 cell cultures were confluented into a monolayer, serum free media containing H2O2 at the final concentration of 200 μmol/L were added, and the cultures were incubated in a thermostatic incubator at 37° C. and 5% CO2 for 24 hr; Sample treatment group: After PC12 cell cultures were confluented into monolayer, the original media were removed, a sample was added to pretreat for 1 hr, followed by H2O2 at a final concentration of 200 μmol/L, then the cultures were incubated in serum-free for 24 hr.

3. Cell Vitality Assay

100 μl MTT solutions at a final concentration of 0.5 mg/ml were added to each well, and the cultures were further incubated at 37° C. and 5% $CO_2$ for 4 h, then the supernatant was discarded. 100 μl DMSO was added to each well and shaken, then OD value of the absorbance was measured at 540 nm. Cell viability= $A_{testing\ well}/A_{normal\ control\ well}*100\%$ Results of Assay PC12 cell viability decreased to 71.94±3.54% which exhibited significant difference (P<0.01) compared to normal control group after hydrogen peroxide injury; and the viability in 0.25, 0.5, 1 u/ml analgecine dosing groups significantly increased compared to model group (P<0.05).

TABLE 4

Protective effects of analgecine on hydrogen peroxide-injured PC12 cells

| Groups | Doses | Cell viability (%) |
| --- | --- | --- |
| Normal control group | — | 100 ± 4.30 |
| Injury model group | 200 uM $H_2O_2$ | 71.94 ± 3.54## |
| Analgecine | 1 U/ml | 80.17 ± 0.64* |
| Analgecine | 0.5 U/ml | 91.53 ± 2.24** |
| Analgecine | 0.25 U/ml | 91.57 ± 0.35** |

The values were expressed as means ± SD, n = 3 for each group.
$P < 0.05$, ##$P < 0.01$ compared to normal group.
*$P < 0.05$, **$P < 0.01$ compared to model group.

Example 3 Protective Effects of Analgecine on Glutamic Acid-Injured Nerve Cells

Experimental Materials

1. Drugs and Reagents

PC12 cells were purchased from Institute of Basic Medical Sciences of Chinese Academy of Medical Sciences; 3-(4,5-Dimethylthiazol-2-yl)-2,5-diphenyltetrazolium bromide (MTT), trypsase, polylysine were purchased from Sigma. Standard fetal bovine serum (FBS), 1640 medium were purchased from Gibco. All other conventional reagents are analytically pure reagents commercially available in China.

2. Instruments

Super clean bench; Fluostar microplate reader (BMG, Germany); Cell incubator (Sanyo, Japan); Refrigerated centrifuge DL-4000B (Shanghai Anting Scientific Instrument Factory); Microscope IX71 (OLYMPUS).

Experimental Method

1. PC12 Cell Culture

PC12 cells were cultured in complete 1640 medium (containing 10% equine serum, 5% fetal bovine serum, 100 U/ml penicillin, 100 μg/ml streptomycin) in a thermostatic incubator at 37° C. and 5% CO2 with the medium changed every 2-3 days.

2. Cell Processing

After PC12 cell cultures were confluented into monolayer, the original media were removed, Mg2+ free-Earle's solution (NaCl 142.6 mmol/L, KCl 5.4 mmol/L, CaCl2) 1.8 mmol/L, $NaH_2PO_4$ 1.0 mmol/L, HEPERS 2.38 mmol/L, Glucose 5.6 mmol/L, pH7.4, 0.5 uM L-gly) containing 1 mM of L-glutamic acid was added. The solution was replaced by serum free 1640 medium after 15 min. Determination was conducted 24 h later. The solution in dosing group was replaced by drug-containing serum free 1640 medium, and determination was conducted after incubation of cells for 24 h.

3 Cell Vitality Assay 100 ul MTT solution at a final concentration of 0.5 mg/ml was added to each well, and the cultures were further incubated at 37° C. and 5% CO2 for 4 h. The supernatant was discarded. 100 μl DMSO was added to each well and shaken, then OD value of the absorbance was measured at 540 nm. Cell viability=$A_{testing\ well}/A_{normal\ control\ well}*100\%$ Results of Assay

TABLE 5

Protective effects of analgecine on glutamic acid injured PC12 cells
PC12 cell viability decreased to 74.76 ± 4.86% after glutamic acid injury, which exhibited significant difference (P < 0.01) compared to normal control group; the viability in 0.25, 0.5, 1 u/ml analgecine dosing group significantly increased compared to model group (P < 0.01).

| Groups | Doses | Cell viability (%) |
| --- | --- | --- |
| Normal control group | | 100 ± 7.15 |
| Injury model group | 200 uM $H_2O_2$ | 74.76 ± 4.86## |
| Analgecine | 1 U/ml | 90.88 ± 5.67** |
| Analgecine | 0.5 U/ml | 93.42 ± 4.13** |
| Analgecine | 0.25 U/ml | 91.69 ± 3.61** |

The values were expressed as means ± SD, n = 4 for each group.
$P < 0.05$, ##$P < 0.01$ compared to normal group.
*$P < 0.05$, **$P < 0.01$ compared to model group.

Examples 4 Effects of Analgecine on Expression or Excretion of ICAM-1 Induced by LPS in the Endothelial Cells of Cerebral Vessels Experimental Materials 1. Drugs and Reagents ICAM-1 ELISA assay kits were purchased from Wuhan Boster Bio-engineering Ltd. Co. Endothelial cell growth fator was provided by Roche. Fetal bovine serum was the product of Gibco. 3-(4,5-Dimethylthiazol-2-yl)-2,5-diphenyltetrazolium bromide (MTT), trypsase, polylysine and lipopolysaccharide (LPS) were purchased from Sigma. Standard fetal bovine serum (FBS), 1640 medium were purchased from Gibco.

2. Instruments

Super clean bench; Fluostar microplate reader (BMG, Germany); Cell culture incubator (Sanyo, Japan); Refrigerated centrifuge DL-4000B (Shanghai Anting Scientific Instrument Factory); Microscope IX71 (OLYMPUS); Zenyth200st UV-Vis spectrophotometer (Anthos Co. Austria).

Experimental Method

1. Culture of Endothelial Cells of the Cerebral Vessels of Rats 1-5 day old neonatal Wistar rats were decapitated. The cortex tissues were harvested, homogenated and filtered before segments of the microvessel on the filter screen were collected. The segments were digested by 0.1% collagenase type VII followed by centrifugation. M199 medium containing 15% fetal bovine serum were added to the precipitate, which was cultured in an incubator at 37° C. and 5% CO2. The cells were digested with 0.25% trypsinase for passage. VIIIF: Ag immunocytochemistry assay was conducted for blood vessel endothelial cell with purity above 95%. Passage 3 of the microvessel endothelial cells is used in this assay.

2. Determination of Secretion of ICAM-1 of Endothelial Cells by ELISA Assay

The endothelial cells of cerebral vessel were cultured in 96-well plate. LPS (10 ug/ml) was added to the wells for stimulation for 24 hrs when the endothelial cells were confluented into monolayer, then ICAM-1 was determined in the cell supernatant. The level of ICAM-1 for each sample was derived from a standard curve.

Results of Assay

After lipopolysaccharide (LPS) injury, ICAM-1 expressed or excreted by the endothelial cells in cerebral vessels exhibited significant difference (P<0.01) compared to the normal control group; the ICAM-1 in 0.25, 0.5, 1 u/ml analgecine dosing groups increased significantly compared to model group (P<0.01).

TABLE 6

Effects of analgecine on expression or excretion of ICAM-1 by the endothelial cells of cerebral vessels in rats

| Groups | Doses | ICAM-1 (pg/ml) |
| --- | --- | --- |
| Normal control group | | 62.34 ± 4.54 |
| Injury model group | LPS (10 ug/ml) | 485.09 ± 12.88## |
| Analgecine | 1 U/ml | 205.54 ± 3.21** |
| Analgecine | 0.5 U/ml | 167.73 ± 25.50** |
| Analgecine | 0.25 U/ml | 179.55 ± 58.43** |

The values were expressed as means ± SD, n = 4 for each group.
P < 0.05, ##P < 0.01 compared to normal group.
*P < 0.05, **P < 0.01 compared to model group.

Examples 5 Effects of Analgecine on Lymphocyte Transformation

Experimental Materials
1. Drugs and Reagents 1640 medium (containing 10% calf serum, double-antibody, glutamine), double distilled water, saline, ConA and PMA were all purchased from Sigma.

2. Animals

Balb/c mice were purchased from Institute of Zoology of Chinese Academy of Medical Sciences.

3. Instruments

Super clean bench; Fluostar microplate reader (BMG, Germany); Cell culture incubator (Sanyo, Japan); Refrigerated centrifuge DL-4000B (Shanghai Anting Scientific Instrument Factory); Microscope IX71 (OLYMPUS); and Zenyth200st UV-Vis spectrophotometer (Anthos Co. Austria).

Experimental Method

1. The spleens of Balb/C mice were collected using conventional method under aseptic condition, and were gently comminuted with a pestle followed by passing through a 200 mesh steel sieve, then washed with 1640 medium once, and centrifuged at 2000 rpm×5 min.

2. The pellets of cells were washed with double distilled water and saline to disrupt erythrocytes, centrifuged, and the supernatant was discarded. The concentration of cells were adjusted to $2×10^6$/ml with 1640 medium, then were placed in 96-well plates at 100 μl/well while ConA (final concentration of 5 ug/ml) or PMA (final concentration of 5 ug/ml) were added at 90 μl/well. The samples or cyclosporin A (final concentration of 50 nM, positive control) were added at 10 μl/well, with wells set up as blank control well (free of the inducer and the drug) or negative control well (inclusion of the inducer, but free of the drug), then incubated at 37° C. and 5% $CO_2$ for 72 h.

3. The supernatant was discarded and 100 μl MTT (final concentration of 0.04%) was added 4 hours before the end of culture. OD was determined at 540 nm at the end of culture.

4. Effects of sample on lymphocyte transformation were expressed as percentage, in which the positive numbers represent improvement of lymphocyte transformation, and negative numbers represent inhibition of lymphocyte transformation. Lymphocyte transformation %=(OD value of sample well−OD value of negative control well)/(OD value of negative control well−OD value of blank control well)× 100%

Results of Assay

The results shown in Table 7 indicated that analgecine has certain inhibitory effects on lymphocyte transformation.

TABLE 7

Effects of analgecine on lymphocyte transformation

| Group | Doses | T-lymphocyte transformation (%) | B-lymphocyte transformation (%) |
| --- | --- | --- | --- |
| Analgecine | 0.5 U/ml | −67.70 | −70.66 |
| | 0.25 U | −68.62 | −19.46 |
| | 0.125 U | −71.76 | −25.86 |

Example 6. Preparation of Antigens for Inoculation

A strong healthy adult Japanese white rabbit weighted 2.5 kg with 3 cm test is was used as a male rabbit for antigen subculture. The scrotum was disinfected with swab soaked with 70% alcohol. The antigen vaccinia virus (vaccinum variolae) Lister (dried cowpox vaccinia virus, produced by the Japanese National Institute of Health Prevention (Tokyo Shinagawa Kamiosaki 2-10-35)) was defrosted and shaken well. 0.2 ml antigen was taken by 1 ml syringe and injected to the central inner part of the testis. The rabbit injected with the antigen was placed back to the specific animal cage which was provided with sufficient drinking water and fodder and observed twice a day. The best result was obtained at 4 days after injection (testis became hardened, swollen, and purple). After cervical dislocation, the scrotum was cleaned with swab soaked with 70% alcohol. The scrotum was dissected and the connective tissue is removed from the testis. The cut-out testis was washed once with normal saline (0.9%) and twice with PBS(−) (80 g sodium chloride, 2 g potassium chloride, 11.5 g sodium dihydrogen phosphate, 2 g potassium dihydrogen phosphate dehydrate, 10 L injectable water). The rinsed testis was blot-dried, weighed, placed in a designated container with ice. Ultimately, the testis was stored in the −80° C. ultra-low temperature refrigerator. The tissue (testis) taken from the refrigerator was softened for 1 hour and then homogenized at low temperature (4° C.). The homogenate mixed with Eagles's medium at 1:1 ratio, which medium comprises 9.4 g Eagle's Powder, 12.5-22 ml 10% sodium bicarbonate, 10 ml glutamine, 1 L injectable water. The mixture was aliquoted and placed in −80° C. ultra-low temperature freezer to freeze for 1 hour. The mixture was taken out and thawed at 37° C. water bath. The freeze and thaw were repeated 3 times. The mixture was centrifuged at low temperature (4° C., 3500 rpm, 20 minutes). The mixture was aliquoted into 10 ml/tube and stored in −80° ultra-low temperature refrigerator.

Example 7. Preparation of Active Agent

Antigen was taken out from the −80° ultra low temperature freezer and placed in 30° incubator to thaw slowly. 5 ml antigen (10^7-10^8 virus/ml) obtained from Example 6 was taken using a 10 ml syringe and mixed with 500 ml PBS(−) well to get the antigen for injection. The back of a healthy mature rabbit (2.75 kg) was shaved and then rubbed with swab soaked with 75% alcohol. The antigen prepared above was used for intradermal injection to the back of the rabbit from left to right. Each injection should be separated by 1.5 cm. Eleven injections were applied from proximal to distal. 5 columns were made on each side. Each injection contains 0.2 ml antigen. Cautions were taken to ensure no leaking, no empty shot, no transdermal injection. The rabbit injected with antigen was housed for 4 days. The lesion was developed well with color changed from red to purplish red, increased skin thickness, subcutaneous edema, edema at hip. After cervical dislocation for euthanasia, the skin was taken within 15 minutes after death. Plastic bag is used to pack the skin and stored in −80° C. freezer until use. The skin (20×20 cm, 200 g) was cut into small pieces of 1 cm square to which 3.5 times the portion of the skin (w/w) amount of 2% phenol solution was added. The solution was flushed with nitrogen for 3 minutes to make it form foam and then sealed. The solution was placed at 4° C. for 72 hours and emulsified before centrifuged. The supernatant was stored and filtered with filter paper No. 5 to obtain a brown Solution A which was then flushed with nitrogen for 3 minutes to make it form foam. Then 1M hydrochloric acid was used to adjust the pH of the Solution A to 5.0 and boiled in water bath for 30 minutes and immediately cooled down to 28° C. afterward. The solution was centrifuged and filtered under low pressure with filter paper No. 5 to obtain Solution B which then was flushed with nitrogen for 3 minutes to make it form foam. Then 1M sodium hydroxide was used to adjust the pH of the solution to 9.2 and boiled in water bath for 30 minutes and immediately cooled down to 28° C. afterward. The solution was filtered under low pressure with filter paper No. 5 and 0.45 μm membrane to obtain Solution C. Flushed the Solution C with nitrogen for 3 minutes to make it form foam. Then 1M hydrochloric acid was used to adjust the pH of the solution to 4.5. Then the solution was flushed with nitrogen for 3 minutes to make it form foam. 40 g activated charcoal was added and stirred continuously at 30° C. for 4 hours. After stopped stirring, let the solution set still for 30 minutes and took the supernatant. The supernatant was filtered under nitrogen-filled environment with filter paper No. 5. Then the activated charcoal was soaked with injectable water (pH 8.0) and rinsed. Filtered under nitrogen-filled environment with filter paper No. 5. Filtrate was discarded and the activated charcoal was saved. 400 ml of injectable water was added to the activated charcoal in a container and flushed with nitrogen to make it form foam. 1M sodium hydroxide was used to adjust pH to 11.0 and kept stirring for 4 hours. Filtered under nitrogen-filled environment with 0.45 μm filter membrane. 40 ml injectable water was added to rinse the activated charcoal to obtain Solution D. 1M hydrochloric acid was used to adjust the pH of Solution D to 6.0 and the container was filled with nitrogen. Then the container was flushed with nitrogen for 5 minutes to make it form foam. The container was sealed and heated to 121° C. and kept for 20 minutes which was cooled to 40° C. or below to obtain Solution E. The Solution E was taken to the reduced pressure distiller and flushed the distiller with nitrogen. The solution was distilled at 60° C. until the volume reached 5 ml and filtered with filter paper No. 5 and 0.2 μm membrane to obtain 5 ml active agent. The active agent contained aspartic acid, threonine, serine, glutamic acid, glycine, alanine, valine, isoleucine, leucine, tyrosine, phenylalanine, lysine, histidine, urocanic acid, uracil, hypoxanthine, xanthine, and thymine. The ranges of various substances stated above (μg/ml) are: 0.3 aspartic acid, 0.2 threonine, 0.5 serine, 1.1 glutamic acid, 0.5 glycine, 0.6 alanine, 0.3 valine, 0.1 isoleucine, 0.3 leucine, 0.4 tyrosine, 0.2 phenylalanine, 0.1 lysine, 0.2 histidine, 18.2 urocanic acid, 9.5 uracil, 1.1 hypoxanthine, 8.6 xanthine, and 2.0 thymine. The agent is colorless liquid with pH about 7.5, UV absorption at 265-275 nm, positive in ninhydrin reaction, negative in tests for various proteins, positive in 3,5-dihydroxy toluene-hydrochloric acid reaction and positive in arsenomolybdate color reaction.

Example 8. Preparation of Active Agent

Antigen was taken out from the −80° ultra low temperature freezer and placed in 30° incubator to thaw slowly. 5 ml antigen (10^7-10^8 virus/ml) obtained from Example 6 was taken using a 10 ml syringe and mixed with 500 ml PBS(−) well to get the antigen for injection. The back of a healthy mature rabbit (2.5 kg) was shaved and rubbed with swab soaked with 75% alcohol. The antigen prepared above was used for intradermal injection to the back of the rabbit from left to right. Each injection should be separated by 1.5 cm. Ten injections were applied from proximal to distal. 5 columns were made on each side. Each injection is 0.2 ml antigen. Cautions were taken to ensure no leaking, no empty shot, no transdermal injection. The rabbit injected with antigen was housed for 3 days. The lesion was developed well with color changed from red to purplish red, increased skin thickness, subcutaneous edema, edema at hip. After cervical dislocation for euthanasia, the skin was taken within 15 minutes after death. Plastic bag is used to pack the skin and stored in −80° C. freezer until use. The skin (18×18, 180 g) was cut into small pieces of 1 cm square to which 2.5 times the portion of the skin (w/w) amount of 2% phenol solution was added. The solution was flushed with nitrogen for 3 minutes to make it form foam. Then the solution was sealed. The solution was placed at 4° C. for 70 hours and emulsified before centrifuged. The supernatant was saved and filtered with filter paper No. 5 to obtain a brown Solution A. The Solution A was flushed with nitrogen for 3 minutes to make it form foam. Then 1M hydrochloric acid was used to adjust the pH of the Solution A to 4.5 which solution was boiled in water bath for 30 minutes and immediately cooled down to 26° C. afterward. The solution was centrifuged and filtered under low pressure with filter paper No. 5 to obtain Solution B. The Solution B was flushed with nitrogen for 3 minutes to make it form foam. Then 1M sodium hydroxide was used to adjust the pH of the solution to 8.7 which solution was boiled in water bath for 30 minutes and immediately cooled down to 26° C. afterward. The solution was filtered under low pressure with filter paper No. 5 and 0.45 μm membrane to obtain Solution C. The Solution C was flushed with nitrogen for 3 minutes to make it form foam.

Then 1M hydrochloric acid was used to adjust the pH of the solution to 4.0. Then the solution was flushed with nitrogen for 3 minutes to make it form foam. 30 g activated charcoal was added and stirred continuously at 25° C. for 4 hours. After stopped stirring, let the solution set still for 30 minutes and took the supernatant. The supernatant was filtered under nitrogen-filled environment with filter paper No. 5. Then the activated charcoal was soaked with injectable water (pH 8.0) and rinsed. Filtered under nitrogen-filled environment with filter paper No. 5. The filtrate was discarded and the activated charcoal was saved. 360 ml of injectable water was added to the activated charcoal in a container and flushed with nitrogen to make it form foam. 1M sodium hydroxide was used to adjust pH to 10.5 and kept stirring for 4 hours. Filtered under nitrogen-filled environment with 0.45 μm filter membrane. Another 45 ml injectable water was added to rinse the activated charcoal to obtain Solution D. 1M hydrochloric acid was used to adjust the pH of Solution D to 5.5 and the container was filled with nitrogen. Then the container was flushed nitrogen for 5 minutes to make it form foam. The container was sealed and heated to 121° C. and kept for 20 minutes then cooled to 40° C. or below to obtain Solution E. The Solution E was taken to the reduced pressure distiller and flushed the distiller with nitrogen. The solution was distilled at 70° C. until the volume reached 5 ml. Filtered with filter paper No. 5 and 0.2 μm membrane to obtain 2 ml active agent. The active agent contained aspartic acid, threonine, serine, glutamic acid, glycine, alanine, valine, isoleucine, leucine, tyrosine, phenylalanine, lysine, histidine, urocanic acid, uracil, hypoxanthine, xanthine, and thymine. The ranges of various substances stated above (μg/ml) are: 0.2 aspartic acid, 0.4 threonine, 0.3 serine, 1.4 glutamic acid, 0.7 glycine, 0.4 alanine, 0.1 valine, 0.3 isoleucine, 0.4 leucine, 0.6 tyrosine, 0.1 phenylalanine, 0.05 lysine, 0.4 histidine, 12.0 urocanic acid, 12.1 uracil, 1.4 hypoxanthine, 5.4 xanthine, and 1.3 thymine. The agent is colorless liquid with pH about 7.0, UV absorption at 265-275 nm, positive in ninhydrin reaction, negative in test for various proteins, positive in 3,5-dihydroxy toluene-hydrochloric acid reaction and positive in arseno molybdate color reaction.

Example 9. Preparation of Active Agent

Antigen was taken out from the −80° ultra low temperature freezer and placed in 30° incubator to thaw slowly. 5 ml antigen ($10^7$-$10^8$ virus/ml) obtained from Example 6 was taken using a 10 ml syringe and mixed with 500 ml PBS(−) well to get the antigen for injection. The back of a healthy mature rabbit (3 kg) was shaved and rubbed with swab soaked with 75% alcohol. The antigen prepared above was used for intradermal injection to the back of the rabbit from left to right. Each injection should be separated by 1.5 cm. Twelve injections were applied from proximal to distal. 5 columns were made on each side. Each injection is 0.2 ml antigen. Cautions were taken to ensure no leaking, no empty shot, no transdermal injection. The rabbit injected with antigen was housed for 4 days. The lesion was developed well with color changed from red to purplish red, increased skin thickness, subcutaneous edema, edema at hip. After cervical dislocation for euthanasia, the skin was taken within 15 minutes after death. Plastic bag is used to pack the skin and stored in −80° C. freezer until use. The skin (22×22 cm, 220 g) was cut into small pieces of 1 cm square to which 2 times the portion of the skin (w/w) amount of 2% phenol solution was added. The solution was flushed with nitrogen for 3 minutes to make it form foam and then sealed. The solution was placed at 4° C. for 72 hours and emulsified before centrifuged. The supernatant was saved and filtered with filter paper No. 5 to obtain a brown Solution A. The Solution A was flushed with nitrogen for 3 minutes to make it form foam. Then 1M hydrochloric acid was used to adjust the pH of the Solution A to 5.5 which solution was boiled in water bath for 30 minutes and immediately cooled down to 30° C. afterward. The solution was centrifuged and filtered under low pressure with filter paper No. 5 to obtain Solution B. The Solution B was flushed with nitrogen for 3 minutes to make it form foam. Then 1M sodium hydroxide was used to adjust the pH of the solution to 9.7 which solution was boiled in water bath for 30 minutes and immediately cooled down to 30° C. afterward. The solution was filtered under low pressure with filter paper No. 5 and 0.45 μm membrane to obtain Solution C. The Solution C was flushed with nitrogen for 3 minutes to make it form foam. Then 1M hydrochloric acid was used to adjust the pH of the solution to 4.8. Then the solution is flushed with nitrogen for 3 minutes to make it form foam. 44 g activated charcoal was added and stirred continuously at 35° C. for 4 hours. After stopped stirring, let the solution set still for 30 minutes and took the supernatant. The supernatant was filtered under nitrogen-filled environment with filter paper No. 5. Then the activated charcoal was soaked with injectable water (pH 8.0) and rinsed. Filtered under nitrogen-filled environment with filter paper No. 5. The filtrate was discarded and the activated charcoal was saved. 440 ml of injectable water was added to the activated charcoal in a container and flushed with nitrogen to make it form foam. 1M sodium hydroxide was used to adjust pH to 11.5 and kept stirring for 4 hours. Filtered under nitrogen-filled environment with 0.45 μm filter membrane. Another 50 ml injectable water was added to rinse the activated charcoal to obtain Solution D. 1M hydrochloric acid was used to adjust the pH of Solution D to 6.5 and the container was filled with nitrogen. Then flushed nitrogen for 5 minutes to make it form foam. The container was sealed and heated to 121° C. and kept for 20 minutes and then cooled to 45° C. or below to obtain Solution E. The Solution E was taken to the reduced pressure distiller and flushed the distiller with nitrogen. The solution was distilled at 55° C. until the volume reached 4 ml. Filtered with filter paper No. 5 and 0.2 μm membrane to obtain 4 ml active agent. The active agent contained aspartic acid, threonine, serine, glutamic acid, glycine, alanine, valine, isoleucine, leucine, tyrosine, phenylalanine, lysine, histidine, urocanic acid, uracil, hypoxanthine, xanthine, and thymine. The ranges of various substances stated above (ug/ml) are: 0.5 aspartic acid, 0.1 threonine, 0.8 serine, 0.7 glutamic acid, 0.3 glycine, 0.9 alanine, 0.4 valine, 0.1 isoleucine, 0.1 leucine, 0.2 tyrosine, 0.4 phenylalanine, 0.2 lysine, 0.1 histidine, 22.5 urocanic acid, 6.5 uracil, 0.7 hypoxanthine, 10.2 xanthine, and 2.5 thymine. The agent is colorless liquid with pH about 8.0, UV absorption at 265-275 nm, positive in ninhydrin reaction, negative in test for various proteins, positive in 3,5-dihydroxy toluene-hydrochloric acid reaction and positive in arsenomolybdate color reaction.

Example 10. Preparation of an Injection

An injection was prepared using the following formulation and the conventional method for injection preparation:

Active agent obtained from Example 7 5 ml

Sodium chloride 2.6 g

Injectable distilled water 300 ml.

Example 11. Preparation of an Injection

An injection was prepared using the following formulation and the conventional method for injection preparation:
Active agent obtained from Example 8 5 ml
Sodium chloride 2.52 g
Injectable distilled water 280 ml.

Example 12. Preparation of Injection

An injection was prepared using the following formulation and the conventional method for injection preparation:
Active agent obtained from Example 9 5 ml
Sodium chloride 2.79 g
Injectable distilled water 310 ml.

Example 13. Preparation of Tablets

A tablet was prepared using the following formulation and the conventional method for tablet preparation:
Active agent obtained from Example 7 50 ml
Lactose 125 mg
Crystalline cellulose 20 g
Magnesium stearate 5 mg.

REFERENCES

The references listed below are incorporated herein by reference in their entireties, but shall not be construed as an admission that such references may be used as prior art for assessing the present invention in any way.
1. Koroshetz W J, and Moskwotz M A. Emerging treatments for stroke in human. Trends Pharmacol Sci. 1996, 17(6): 227-233.
2. Higashida R T, Furlan A J, Roberts H, Tomsick T, Connors B, Barr J, Dillon W, Warach S, Broderick J, Tilley B, Sacks D. Trial design and reporting standards for intra-arterial cerebral thrombolysis for acute ischemic stroke. Stroke. 2003, 34: 109-137.
3. Feng Y P. Pathophysiology of ischemic stroke and status of drug intervention. Acta Pharm Sin. 1999, 34: 72-78.
4. Fisher M, Bogosky J. Further evaluation toward effective therapy for acute ischemic stroke. JAMA. 1998, 279: 1298-1303.
5. Longa E Z, Weinstein P R, Carlson S, Cummins R. Reversible middle cerebral artery occlusion without craniectomy in rats. Stroke. 1989, 20: 84-91.
6. Maier C M, Ahern K, Cheng M L et al. Optimal depth and duration of mild hypothermia in a focal model of transient cerebral ischemia: effects on neurologic outcome, infarct size, apoptosis, and inflammation. Stroke. 1998, 29: 2171-2180.
7. Bederson J B, Pitts L H, Tsuji M et al., Rat middle cerebral artery occlusion: evaluation of the model and development of a neurologic examination. Stroke. 1986, 17:472-476.
8. Belayev L, Alonso O F, Busto R, Zhao W, Ginsberg M D. Middle cerebral artery occlusion in the rat by intraluminal suture: Neurological and pathological evaluation of an improved model. Stroke. 1996, 27: 1616-1622.
9. Bederson J B, Pitts L H, Germano S M. Evaluation of 2,3,5-triphenyltetrazolium chloride as a stain for detection and quantification of experimental cerebral infarction in rats. Stroke. 1986, 17:1304-1309.
10. Bradford, M M. A rapid and sensitive method for the quantition of microgram quantities of protein utilizing the principle of protein-dye binding. Anal. Biochem. 1976, 72: 248-252.
11. Okawa M, Kinjo J, Nohara T; DPPH (1,1-diphenyl-2-picrylhydrazyl) radical scavenging activity of flavonoids obtained from some medicinal plants. Biol Pharm Bull. 2001; 24(10):1202-5.
12. Leizhimeing, Xuebin, Zhaoxilong, et al., Determination of the proliferation of lymphocyte by MTT color reaction assay using 721 spectrophotometer, Current Immunology, 1990; 10(3): 172.
13. E merich DF, Dean R L, Bartes R T, et al., The role of leukocytes following cerebral ischemia: pathogenic variable or bystander reaction to emerging infarct. Exp Neurol, 2002, 173:168.

The invention claimed is:

1. A method for protecting nerve cells, improving $H_2O_2$-induced injury of PC12 cells, or improving glutamic acid-induced injury of PC12 cells in an acute cerebrovascular disease, the method comprising administering to a subject in need thereof, at 2 hours, 6 hours, 20 hours, 24 hours, and 47 hours after onset of acute cerebral ischemia, a therapeutically effective amount of a composition comprising:
   an analgesic containing an active agent and a pharmaceutically acceptable excipient, the pharmaceutically acceptable excipient comprising at least one of a stabilizer, emulsifier, adjuvent, binding agent, disintegrant and a wetting agent;
   wherein said active agent contains aspartic acid, threonine, serine, glutamic acid, glycine, alanine, valine, isoleucine, leucine, tyrosine, phenylalanine, lysine and histidine, and contains urocanic acid, uracil, hypoxanthine, xanthine, and thymine;
   wherein said active agent is a colorless or a pale yellow liquid with a pH between 7.0 and 8.0, UV absorption at 265-275 nm, positive in ninhydrin reaction, positive in 3,5-dihydroxy toluene-hydrochloric acid reaction and positive in arsenomolybdate color reaction;
   wherein the composition is prepared by:
   a) collecting a pox skin tissue from vaccinia virus (Vaccinum variolae) Lister strain-inoculated rabbit;
   b) cutting the collected tissue into pieces, to which 2.5 to 3.5 times the portion of the skin (w/w) amount of 2% phenol aqueous solution is added, and obtaining a solution A by soaking, centrifugation and filtration;

c) obtaining a solution B by adjusting a pH of the solution A to become more acidic, boiling and then centrifuging and filtering solution B;

d) obtaining a solution C by adjusting a pH of the solution B to become more alkaline, and boiling followed by filtration;

e) obtaining a solution D by adjusting a pH of the solution C to become more acidic, to which an adsorbent is added, and soaking, filtering, and eluting the adsorbent with water in an alkaline environment;

f) obtaining a solution E by adjusting the solution D to become more acidic, and heating followed by cooling; and g) concentrating the solution E under reduced pressure and filtration; and wherein said acute ischemic cerebrovascular disease is selected from the group consisting of cerebral embolism, transient cerebral ischemia attack, cerebral thrombosis, cerebral arteriosclerosis, cerebral arteritis, steal syndrome of cerebral artery, cranial venous sinus and venous thrombus.

2. The method of claim 1, wherein the administration of the composition protects the nerve cells by increasing their viability.

3. The method of claim 1, wherein the treatment of said disease occurs by improving neural function, decreasing cerebral infarction areas, decreasing the level of lactic acid in brain tissues or increasing the activity of SOD.

4. The method of claim 1, wherein the subject is human.

5. The method of claim 1, wherein, prior to step c), the solution A is flushed with nitrogen to cause the solution A to form a foam.

6. The method of claim 1, wherein adjusting solution A to become more acidic comprises adjusting the pH to approximately 5.0 with 1M hydrochloric acid.

7. The method of claim 1, wherein adjusting solution B to become more alkaline comprises adjusting the pH to approximately 9.2 with 1M sodium hydroxide.

8. The method of claim 1, wherein adjusting solution C to become more acidic comprises adjusting the pH to approximately 4.5 with 1M hydrochloric acid.

9. The method of claim 1, wherein the adsorbent of step e) comprises activated charcoal.

10. The method of claim 1, wherein adjusting solution E to become more acidic comprises adjusting the pH to approximately 4.5 with 1M hydrochloric acid.

11. The method of claim 1, wherein the active agent comprises approximately: 0.3 μg/ml aspartic acid, 0.2 μg/ml threonine, 0.5 μg/ml serine, 1.1 μg/ml glutamic acid, 0.5 μg/ml glycine, 0.6 μg/ml alanine, 0.3 μg/ml valine, 0.1 μg/ml isoleucine, 0.3 μg/ml leucine, 0.4 μg/ml tyrosine, 0.2 μg/ml phenylalanine, 0.1 μg/ml lysine, 0.2 μg/ml histidine, 18.2 μg/ml urocanic acid, 9.5 μg/ml uracil, 1.1 μg/ml hypoxanthine, 8.6 μg/ml xanthine, and 2.0 μg/ml thymine.

* * * * *